(12) United States Patent
Suwalski et al.

(10) Patent No.: US 10,893,898 B2
(45) Date of Patent: Jan. 19, 2021

(54) CRYOAPPLICATOR FOR MINIMALLY INVASIVE SURGICAL CARDIAC ABLATION

(71) Applicant: Medidata Sp. z o.o., Warsaw (PL)

(72) Inventors: Piotr Suwalski, Warsaw (PL); Sebastian Stec, Warsaw (PL); Sanjeev Choudhary, Warsaw (PL)

(73) Assignee: MEDIDATA SP. ZO.O, Warsaw (PL)

( * ) Notice: Subject to any disclaimer, the term of this patent is extended or adjusted under 35 U.S.C. 154(b) by 215 days.

(21) Appl. No.: 14/975,521

(22) Filed: Dec. 18, 2015

(65) Prior Publication Data

US 2017/0086900 A1    Mar. 30, 2017

(30) Foreign Application Priority Data

Sep. 24, 2015  (EP) .................................... 15002754

(51) Int. Cl.
*A61B 18/02* (2006.01)
*A61M 25/00* (2006.01)
*A61B 18/00* (2006.01)

(52) U.S. Cl.
CPC ......... *A61B 18/02* (2013.01); *A61M 25/0041* (2013.01); *A61B 2018/00023* (2013.01); *A61B 2018/00095* (2013.01); *A61B 2018/00101* (2013.01); *A61B 2018/00351* (2013.01); *A61B 2018/00357* (2013.01); *A61B 2018/00363* (2013.01); *A61B 2018/00577* (2013.01); *A61B 2018/0212* (2013.01); *A61B 2018/0262* (2013.01); *A61M 2025/0006* (2013.01)

(58) Field of Classification Search
CPC .......... A61B 18/02; A61B 2018/00101; A61B 2018/00351; A61B 2018/00577; A61B 2018/0212; A61B 2018/0262
See application file for complete search history.

(56) References Cited

U.S. PATENT DOCUMENTS

| 3,859,986 | A | * | 1/1975 | Okada | A61B 1/00098 600/104 |
|---|---|---|---|---|---|
| 5,833,685 | A | * | 11/1998 | Tortal | A61B 18/02 606/23 |
| 2004/0044350 | A1 | * | 3/2004 | Martin | A61B 17/00234 606/139 |
| 2005/0224086 | A1 | * | 10/2005 | Nahon | A61B 18/02 128/899 |
| 2007/0149960 | A1 | * | 6/2007 | Wittenberger | A61B 18/02 606/23 |

(Continued)

FOREIGN PATENT DOCUMENTS

| EP | 0 741 546 A1 | 11/1996 |
|---|---|---|
| PL | 65217 | 12/2010 |

(Continued)

*Primary Examiner* — Lee S Cohen
*Assistant Examiner* — Tigist S Demie
(74) *Attorney, Agent, or Firm* — Brooks Kushman P.C.

(57) ABSTRACT

The cryoapplicator for minimally invasive surgical cardiac ablation includes a fastening part, an insulation part and an effector tip. A pin is connected with the fastening part on one end, and with the effector tip on the second end. The effector tip is bent by 60° to 90° angle in the side view in relation to pin longitudinal axis, and by 5° to 60° angle in the top view. A thermal insulation cover is located on the pin with the possibility to slide along the longitudinal axis.

12 Claims, 1 Drawing Sheet

(56) References Cited

U.S. PATENT DOCUMENTS

| | | | | |
|---|---|---|---|---|
| 2009/0292279 A1* | 11/2009 | Bliweis | ............... | A61B 18/02 606/21 |
| 2010/0069901 A1* | 3/2010 | Policewicz | ............ | A61B 18/02 606/23 |
| 2011/0184402 A1* | 7/2011 | Baust | ................... | A61B 18/02 606/23 |
| 2013/0006232 A1* | 1/2013 | Pellegrino | ........... | A61B 17/3472 606/33 |
| 2014/0066914 A1 | 3/2014 | Lafontaine | | |
| 2014/0276700 A1* | 9/2014 | McKay | ............. | A61B 18/0218 606/21 |

FOREIGN PATENT DOCUMENTS

| | | |
|---|---|---|
| WO | 01 19270 A1 | 3/2001 |
| WO | 2013 0013098 A1 | 1/2013 |

* cited by examiner

CRYOAPPLICATOR FOR MINIMALLY INVASIVE SURGICAL CARDIAC ABLATION

CROSS-REFERENCE TO RELATED APPLICATIONS

This application claims the benefit of European Patent Application No. EP 15002754.8 filed Sep. 24, 2015, the disclosure of which is hereby incorporated in its entirety by reference herein.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The subject of the invention is the cryoapplicator for minimally invasive surgical cardiac ablation designed for local freezing of tissues, especially heart tissues during cardiac surgery. Invention is designed to perform cryoablation of the atria in order to treat cardiac arrhythmias, especially atrial fibrillation. The invention is intended for endo- and epicardial ablation mainly by minithoracotomy.

2. Description of Related Art Including Information Disclosed Under 37 CFR 1.97 and 37 CFR 1.98.

Surgical ablation of so called accompanying atrial fibrillation is accepted as a treatment standard while conducting different procedures of medical cardiac interventions (most often mitral valve repair or replacement). The method is recommended in Polish, European and American treatment guidelines of renowned associations of cardiology and cardiac surgery.

From the description of protection right PL 65217 Y1 there is known the utility model which discloses cardiac surgery device using liquid nitrogen with set of Suwalski cardiac surgery cryoapplicators. Cryoapplicators disclosed in PL 65217 Y1 description consist of a fastening part, an insulation part and an effector tip. Each fastening part mounted in fastening sleeve slot has identical shape and cross-section. The fastening part has a form of two sleeves wherein one exhibits diameter B and the second, which is located on the end of the cryoapplicator, exhibits diameter A, i.e. diameter of the fastening element of the first internal tube of supply line. The fastening part mounted in cryoapplicator slot is ended with two rings with small external radius difference. The effector tip of the first cryoapplicator is formed as an arch fragment and is slightly tilted. The effector tip of the second cryoapplicator is also formed as an arch fragment but is shorter than the first tip. The effector tip of the third cryoapplicator has greater diameter than the others and is bent at an angle in relation to the insulation part. The effector tip of the fourth cryoapplicator is formed as an arch fragment and is longer than the first and second tip. The effector tip of the fifth cryoapplicator is T-shaped.

A drawback of the aforementioned cryoapplicator is that it does not enable appropriate operation during minimally invasive surgery, that is with access to the heart by so called minithoracotomy, that is with significantly limited access in other thorax locations. Furthermore, it comprises more than one effector tip.

There is also known a cryotherapy device from US 2014066914 consisting of a bent effector tip ended with ablation needle. The refrigerant is liquid nitrogen, nitrous oxide ($N_2O$), carbon dioxide, ($CO_2$), chlorodifluoromethane, polydimethyisiloxane, ethyl alcohol, chlorofluorocarbons or other suitable fluid. This invention describes a piercing catheter ('needle-like ablation tip'), which acts by heart tissue puncturing using special needles. It is an intramuscular cryoablation, not an epicardial one. The Joule-Thomson phenomenon, gas conversion associated with rapid decompression of highly-compressed gas to low-pressure chamber (e.g. $CO_2$, $N_2O$ etc.) giving instant temperature drop, is used to acquire low temperature.

BRIEF SUMMARY OF THE INVENTION

The cryoapplicator for minimally invasive surgical cardiac ablation according to the invention consists of a fastening part, an insulation part and an effector tip. It is characterised in that a pin (1) is connected with the fastening part (2) on one end, and with the effector tip on the second end (3), wherein the effector tip (3) is bent by 60° to 90°, preferably 75° to 90° angle in the side view in relation to pin longitudinal axis; while in the top view by 5° to 60° angle, preferably 10° to 45°. Additionally, a thermal insulation cover (4) is located on the pin (1) with the possibility to slide along the longitudinal axis. The effector tip shape enables carrying out of other applications after rotation and the mobility of thermal insulation cover ensures adjustment of exposed cold part of cryoapplicator.

In a preferable variant, a thermal insulation cover (4) is shorter than the pin (1). In another preferable variant, the thermal insulation cover (4) is ended with a ring (5) with a diameter greater than its middle part. In another preferable variant, the thermal insulation cover (4) is ended with a truncated cone (6). In another preferable variant, the thermal insulation cover (4) is made of polytetrafluoroethylene. In another preferable variant, the pin (1) is made of acid-proof steel, especially 11-118N9T steel. In another preferable variant, the effector tip (3) is made of gold and copper or gold and aluminum alloy.

Aim of the invention. The aim of the invention and also the technical obstacle to solve was obtaining of a low-pressure cryoapplicator for minimally invasive surgery, thus with access to the heart using minithoracotomy and not a typical sternotomy, that is not in the front of the thorax but on the right side under the armpit. Besides, a high number of the effector tips posed a problem. The technical problem is difficult to solve, because left and right atria are three-dimensional anatomical forms with highly complex spatial structure. Changed angle of access and also increased distance from integument (surgical wound) in comparison to sternotomy (classical access) require a completely new concept. It should be also noted that available space is highly limited, since average atrium size is about 3 to 6 cm. Furthermore, a limited minithoracotomy surgical wound in the integument is about 4-5 times smaller than during sternotomy and it refers to the length and the width.

Beneficial effects. An advantage of the cryoapplicator according to the invention is that it is possible to perform a surgery by minithoracotomy with only one effective tip instead of few, as was in the case of the utility model PL 65217 Y1, by bending of the effector tip in two planes by angle disclosed in the present application and due to a possibility to move the thermal insulation cover. Beneficial effect is caused by a simultaneous adjustment of the effector tip shape to the shape of left and right atrium (giving appropriate accession angle) with simultaneous possibility to cover or uncover cold parts of cryoapplicator. Axial mobility of thermal insulation cover relative to the pin enables dynamic adjustment of cover location to the changing anatomical conditions during surgery, depending both on the structure of specific patient and on the application in a specific anatomical location during the whole ablation procedure (the procedure consist of few applications using cryoapplicator within left and right atrium) and simultaneously without increasing of the diameter of the penetration part in places where it can hamper or make ablation impossible on small, few centimeter area. Moreover, thermal insulation cover prevents pin icing increasing safety of the procedure (random freezing of other tissues).

Bending of the effector tip is adjusted in such a way that only clockwise or anti-clockwise rotation of cryoapplicator enables precise performance of a next application (after rotation, the bending adapts to the new application position) without the need to remove cryoapplicator from thorax.

Operating with the effector tip according to the invention with simultaneous possibility of axial sliding of thermal insulation cover synergistically influences cryoablation effect and in consequence:
  shortens operation time;
  does not require effector tip replacement (thus, does not distract cardiac surgeon);
  facilitates manual control over cryoapplicator because it is easier to learn how to manipulate with one effector tip than with few of them, which in consequence reduces operation risk;
  ensures good effector tip abutting and thereby ensures continuity of ablation lines.

BRIEF DESCRIPTION OF THE SEVERAL VIEWS OF THE DRAWINGS

The cryoapplicator for minimally invasive surgical cardiac ablation is demonstrated in the example illustrated in the drawings.

DETAILED DESCRIPTION OF THE INVENTION

Figure 1:
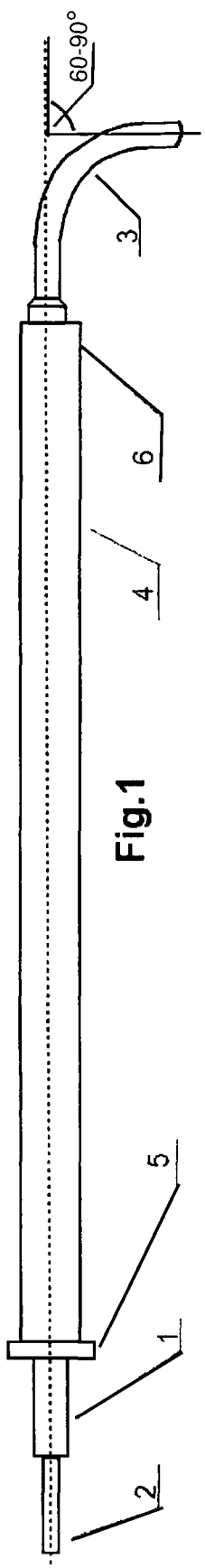
FIG. 1 presents a side elevation view of cryoapplicator according to the invention with longer thermal insulation cover.
Figure 2:
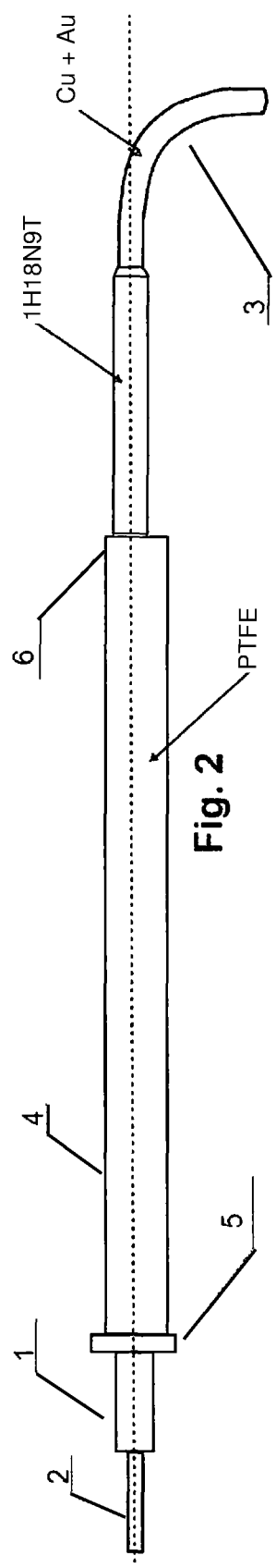
FIG. 2 presents a side elevation view of the cryoapplicator according to the invention with shorter thermal insulation cover.
Figure 3:
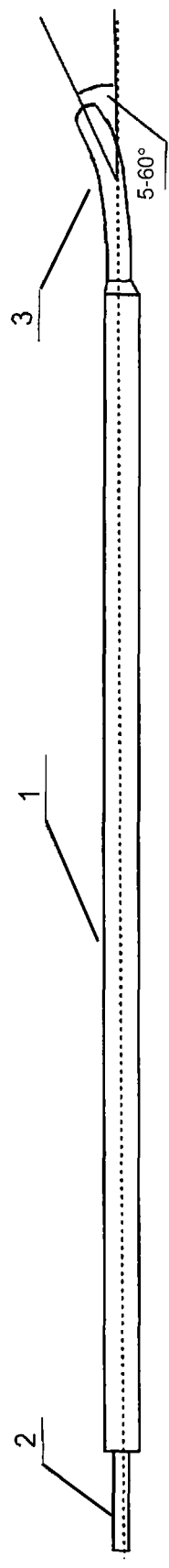
FIG. 3 presents a top plan view of the cryoapplicator according to the invention without a thermal insulation cover.

The cryoapplicator for minimally invasive surgical cardiac ablation according to the invention consists of the fastening part, the insulation part and the effector tip. The pin (1) made of acid-proof steel (preferably 1H18N9T steel) is connected with the fastening part (2) on one end, and with the effector tip (3) made of gold and copper alloy on the second end. Due to the use of copper, this alloy provides good thermal conductivity and the use of gold significantly reduces oxidation. Additionally, aluminum can be used instead of copper. However, the effector tip (3) is bent by 60° to 90° angle in the side view in relation to pin (1) longitudinal axis, and by 5° to 60° angle in the top view. Still, most ergonomic were 75° to 90° angle ranges for bending in the side view in relation to pin (1) longitudinal axis and 10° to 45° in the top view. Additionally, a thermal insulation cover (4) is located on the pin (1) with the possibility to slide along the longitudinal axis. The thermal insulation cover (4) is optionally equally long as the pin (1) or is shorter, which enables moving of thermal insulation cover (4) and thus uncovering of the pin (1) or covering of the effector tip (3). Additionally, thermal insulation cover (4) is ended with truncated cone (6) in order to obtain smooth change in the diameter.

Liquid nitrogen is the refrigerant flowing through cryoapplicator therefore thermal insulation cover (4) is made of polytetrafluoroethylene (PTFE) which besides its properties as a thermal insulator has also lubricating properties which are preferable during manipulation of thermal insulation cover (4) during cardiac surgery. In order to disable the displacement of thermal insulation cover further in the device supplying cryoapplicator with refrigerant, thermal insulation cover (4) is closed with the ring (5) with a diameter bigger than its middle part.

Application example. The invention is intended for surgical ablation of the atria. Ablation is based on the controlled generation of scars with appropriate shape within the atria which scars modify abnormal (in case of arrhythmia) sequence of electrical impulses in the heart. The use of cryoapplicator according to the invention implies performing of so called cryoablation, that is generation of aforementioned scars by applying of the cryoapplicator with aforementioned shape to the atrium tissue, which by generation of low temperature induces local death of cardiomyocytes and scars formation (technique used for decades in many fields of medicine, e.g. dermatology, surgery, oncology).

Generation of low temperature is carried out by flowing of low pressure nitrogen, that comes from the generator, through the cryoapplicator which leads to cooling down of the effector tip (3) to the temperature from minus 180° C. to minus 160° C. Desired temperature range is controlled by thermistors positioned in controlling unit of liquid nitrogen generator. One application lasts about 1 minute. About 2-4 applications are needed to generate ablation line therapeutic pattern. The use of the invention does not need any additional incisions on the heart or other tissues. Whole cardiac surgery is prolonged for 12-15 minutes. In a number of publications concerning ablations using different energy sources, including those with low temperature, there was reported no negative effect on general results of principal cardiac surgery with simultaneous high therapeutic effectiveness.

Shape of the invention enables its usage during typical operation by sternotomy but it is adjusted especially to the minimally invasive operations by minithoracotomy. It relates to the length of the whole device and especially to the appropriate shape of the effective tip (3), adapted to the shape of left and right atrium from specific accession angle, and to the appropriate diameter thereof in order to perform application with required width.

A cryoapplicator was made of metal alloys which are resistant to deformations, decay or change in physical or chemical properties under low temperature. Liquid nitrogen flow through cryoapplicator is carried out using low-pressure method. Furthermore, the invention is electrically neutral.

We claim:

1. A cryoapplicator for minimally invasive surgical cardiac ablation, said cryoapplicator comprising:
    a fastening part;
    a pin extending along a longitudinal axis and having a first end and a second end;
    an insulation part; and
    a pre-bent effector tip, wherein said first end of said pin connects with said fastening part, wherein said second end of said pin connects with said effector tip, wherein said effector tip is pre-bent by a 60° to 90° angle along a first plane relative to said longitudinal axis, wherein said effector tip is also pre-bent by a 5° to 60° angle along a second plane relative to said longitudinal axis, wherein said insulation part is comprised of a thermal insulation cover located on said pin in a slideable relationship along said longitudinal axis of said pin between a first configuration corresponding to said effector tip in both a first application position and a second application position and a second configuration corresponding to said effector tip in a rest position, said thermal insulation cover being shorter than said pin, and wherein said pin and said pre-bent effector tip are collectively rotatable such that said pin is rotatable within said insulating part.

2. The cryoapplicator, according to the claim 1, wherein said effector tip is bent by a 10° to 45° along the second plane.

3. The cryoapplicator, according to claim 1, wherein said effector tip is bent by 75° to 90° along the first plane.

4. The cryoapplicator according to claim 1, wherein said thermal insulation cover has a ring on an end part, said ring having a diameter greater than a middle part of said thermal insulation cover.

5. The cryoapplicator according to claim 4, wherein said thermal insulation cover has a truncated cone on another end part.

6. The cryoapplicatory, according to claim 1, wherein said thermal insulation cover is comprised of polytetrafluoroethylene.

7. The cryoapplicator, according to claim 1, wherein said pin is comprised of acid-proof steel.

8. The cryoapplicatory, according to claim 1, wherein said effector tip is comprised of gold and copper alloy.

9. The cryoapplicator, according to claim 1, wherein said pin is comprised of 1H18N9T steel.

10. The cryoapplicator, according to claim 1, wherein said effector tip is comprised of gold and aluminum alloy.

11. The cryoapplicator, according to claim 1, wherein said first plane is non-parallel with said second plane.

12. The cryoapplicator, according to claim 11, wherein said first plane is perpendicular to said second plane.

* * * * *